United States Patent [19]
Longacre

[11] Patent Number: 5,926,270
[45] Date of Patent: Jul. 20, 1999

[54] SYSTEM AND METHOD FOR THE REMOTE DETECTION OF ORGANIC MATERIAL IN ICE IN SITU

[75] Inventor: Jacob R. Longacre, Voluntown, Conn.

[73] Assignee: The United States of America as represented by the Secretary of the Navy, Washington, D.C.

[21] Appl. No.: 08/954,092

[22] Filed: Oct. 14, 1997

[51] Int. Cl.[6] ..................................... G01N 21/64
[52] U.S. Cl. ..................... 356/318; 356/417; 250/458.1
[58] Field of Search .................... 356/317, 318, 356/417; 250/458.1, 459.1, 461.1

[56] References Cited

U.S. PATENT DOCUMENTS 5,257,085  10/1993  Ulich et al. .............................. 356/318
5,379,103  1/1995  Zigler ...................................... 356/318

Primary Examiner—F. L. Evans
Attorney, Agent, or Firm—Michael J. McGowan; Prithvi C. Lalll; Robert W. Gauthier

[57] ABSTRACT

A system for remotely detecting organic material in a volume, such as an ice layer, in situ, includes a light source, an optical receiver and a control subsystem. The light source generates a laser light beam and directs the generated laser beam at the volume. If organic material is present in the volume, the optical receiver detects fluorescent light components from the volume generated by the organic material in response to the laser light beam generated by the light source. The control subsystem controls the operations of the light source and the optical receiver.

14 Claims, 1 Drawing Sheet

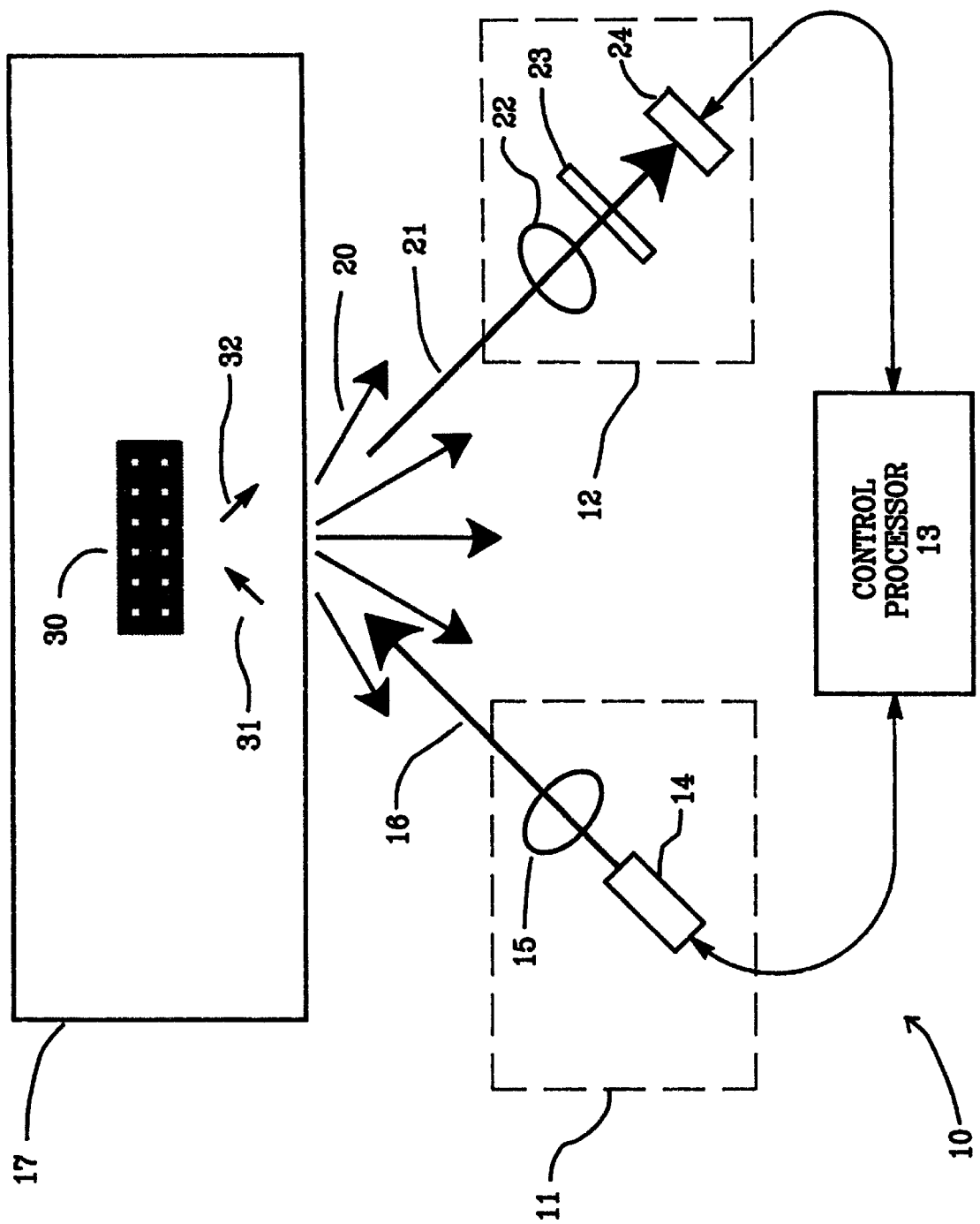

5,926,270

SYSTEM AND METHOD FOR THE REMOTE DETECTION OF ORGANIC MATERIAL IN ICE IN SITU

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

1. Field of the Invention

The invention relates generally to the field of remote detection of organic materials and more particularly to systems and methods of detecting the presence of organic materials, including life forms, in situ in ice.

2. Description of the Prior Art

A system for remotely detecting the existence of and analyzing organic materials, including life forms, in ice in situ can have a number of uses. For example, such a system could be used to determine the presence and quantity of organic materials and contaminants in ice. Additionally, such a system could be used to map biological communities on the underside of or within ice and conduct in situ bio-optical variability measurements. Such measurements, combined with environmental measurements such as temperature, salinity, ambient light, and so forth, may be useful in determining the life cycles and requirements of different organisms and organic materials, and effects thereon caused by human encroachment.

Several arrangements have been developed for detecting organic materials. For example, U.S. Pat. No. 3,961,187 to Barringer discloses a method for remotely sensing hydrocarbon seeps by bioluminescence of hydrocarbons, bacteria and other microorganisms. U.S. Pat. No. 3,449,571 to Hoerman et al. discloses a method for medical sampling using phosphorescence to identify microorganisms. U.S. Pat. No. 3,470,373 to Brewer et al. discloses a method of identifying microorganisms by phosphorescence. U.S. Pat. No. 4,293,225 to Wheaton et al. discloses a method for measuring fluorescence in situ in seawater. U.S. Pat. No. 5,128,882 to Cooper et al. discloses a method of measuring contamination in situ in soil via fluorescence by using a soil penetrometer to probe the soil. However, none of these references can remotely detect organic material in situ in ice. Thus, what is needed is a system for the remote detection of organic material in ice in situ.

SUMMARY OF THE INVENTION

It is therefore an object of the invention to provide a system and method for the remote detection of organic material in ice in situ.

In brief summary, the invention provides a system for remotely detecting organic material in a volume, such as an ice layer, in situ, employing a light source, an optical receiver and a control subsystem. The light source generates a laser beam which is directed at the volume to be interrogated. If organic material is present in the volume, the optical receiver will detect fluorescent light components from the volume generated by the excitation of organic material by the laser light beam generated by the light source. The control subsystem controls the operations of the light source and the optical receiver.

BRIEF DESCRIPTION OF THE DRAWINGS

A more complete understanding of the invention and many of the attendant advantages thereto will be readily appreciated as the invention becomes better understood by reference to the following description taken in conjunction with the sole accompanying drawing which shows a schematic diagram depicting an illustrative system for the remote detection of organic material in ice in situ, constructed in accordance with the invention.

DESCRIPTION OF THE PREFERRED EMBODIMENT

Referring now to the sole FIGURE, there is shown a schematic diagram depicting a system 10, constructed in accordance with the invention, for facilitating the remote detection of organic material in ice in situ. The system 10 includes a light source 11 and an optical receiver 12 under control of a control processor 13. The light source 11 includes a laser beam generator 14 and an optical subsystem 15. Under control of the control processor 13, the laser beam generator 14 generates a laser beam, represented by a ray identified by reference numeral 16 and the optical subsystem 15 directs the laser beam at a portion of ice 17 to be examined for organic material. In the FIGURE an item of organic material, which may include life forms such as algae, is embedded in the ice layer, represented by reference numeral 30.

The ice 17 generally reflects and scatters portions of the incident light beam 16. In addition, a portion of the incident beam 16, identified by reference numeral 31, will refract into the ice layer and impinge upon organic material 30. The organic material 30 will, when impacted by the incident beam, fluoresce, and radiate light, identified by reference numeral 32, at predetermined wavelengths as determined by their composition. The light as reflected and scattered by the ice layer 17, as well as the radiated light 32 generated by the organic materials are represented by rays generally identified by reference numeral 20.

A portion of the scattered reflected rays, identified by reference numeral 21, impinges on the optical receiver 12 and, in particular, on an optical collection subsystem 22, which directs and focuses the portion of the reflected rays received thereby through an optical filter 23 onto an optical detector 24. The optical collection subsystem 22 may include any convenient arrangement for collecting the scattered reflected rays 21 and directing (transferring) the received rays to filter 23 including a lens arrangement and/or mirrors, and may also include a fiber optic transmission system to direct the rays 21 to filter 23.

The optical filter 23 will filter out of the light incident thereon components of the light which do not conform to the wavelengths at which organic material and life forms are known to fluoresce. Thus, if, as is typical, the laser beam generated by laser beam generator 14 is at a wavelength that is different from the wavelength at which organic materials and life forms fluoresce, the optical filter 23 can assist in filtering out components comprising the reflections of the laser beam, leaving the components corresponding to the fluorescent material 30 in the ice layer 17. The filtered light passed by filter 23 within the optical sensor is detected by the optical detector 24, which can generate a signal to be coupled to the control processor 13 for analysis.

The optical detector 24 may be responsive to light of a particular one of a number or range of wavelengths at which organic material may fluoresce. Alternatively, where a large number or fluorescent wavelengths are being investigated, if the particular fluorescent wavelength or wavelengths is unknown, or if a fluorescent spectrum is being investigated, the optical detector 24 may comprise a spectrometer that is sensitive to wavelengths across a predetermined or variable spectrum. Additionally, the optical receiver may include a fiber optic transmission line and/or alignment mirrors (not shown) to carry or direct the filtered rays to the optical detector 24 as required by the selected optical path.

The particular types of laser beam generators 14 which are used in the system 10, and the wavelength of the laser beam which they generate, will depend on the particular types of organic materials to be investigated in the layer 17. Illustrative laser beam generators 14 which will find utility in system 10 include UV laser sources, blue and blue-green sources such as Argon lasers, or a frequency doubled NdYAG laser or a frequency-doubled NdYLF laser, which generate laser light at wavelengths of approximately 532 and 523 nanometers, respectively. The laser beam generator 14 may generate a continuous beam (that is, the generator may comprise a so-called "continuous wave" or "CW" laser beam generator) or it may generate laser beam pulses. Generally, a pulsed laser beam generator 14 can generate laser beam pulses having higher energy levels than continuous wave generates, which can enable a higher level of fluorescent excitation of organic material 30 in the ice layer 17. In addition, a pulsed laser beam can be useful in detecting organic material at a particular point in the ice layer 17, by enabling the optical detector 24 to detect fluorescence at a particular time following transmission of a pulse, the time being selected to conform to the propagation delay along the path from the laser beam generator 14 to the particular point and the particular point to the optical detector 24.

The control processor 13 can include any digital computer system or other arrangement for controlling the light source 11 to generate and transmit the laser beam 16 at a selected volume of ice 17, and/or for controlling the optical receiver 12 to receive and analyze the rays 21 to determine whether organic material 17 is present. Depending on the particular environment in which the system 10 is to be used, for example, if the light source 11 and optical receiver 12 are in fixed locations, a control processor 13 may not need to be provided.

The types and concentrations of organic materials that are embedded in the layer 17 can be identified by the wavelengths and relative intensities of the fluorescent light represented by ray 21. The location of the particular portion of layer 17 that is under investigation (the interrogation volume) at any point in time corresponds generally to the point of intersection of incident ray 16, ray 21 (generally, along the optical axis of the optical subsystem 12). The interrogation volume can be easily redefined by modifying the alignment of the incident beam 16 and/or the field of view of the optical receiver 12. Additionally, the interrogation volume can be defined temporally by employing a pulsed laser source and comparing pulse emission and receive times or by gating the optical receiver 12 to only accept pulses for a certain time.

The invention provides a number of advantages. In particular, it provides a system 10 that can remotely measure the fluorescence of organic materials in ice in situ. This can be particularly advantageous in investigations performed, for example, in studying life forms embedded in ice in an ocean environment. The invention can also find utility in connection with detection and characterization of pollutants and contaminants in connection with transparent or translucent materials that have, for example, purity requirements, and determining exact concentrations and ratios of organic solutions.

The preceding description has been limited to a specific embodiment of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed is:

1. A system for remotely detecting organic material in a volume in situ, said system comprising:

a light source for generating a laser light beam and directing the generated laser beam at said volume in a specified direction;

an optical receiver for detecting, if organic material is present in said volume, fluorescent light components from said volume generated by said organic material in response to the laser light beam generated by said light source; and a control subsystem for controlling said light source and said optical receiver, the control subsystem further localizing said organic material within said volume by controlling the direction of the generated beam, a field of view of the optical receiver and timing of the laser light beam.

2. A system as defined in claim 1 in which said light source comprises:

a laser beam generator for generating a laser beam; and focusing optics for focusing said laser beam as said laser light beam on said volume.

3. A system as defined in claim 2 in which said laser beam generator includes a selected one of a frequency doubled NdYAG laser having a wavelength of approximately 532 nanometers and a frequency-doubled NdYLF laser having a wavelength of approximately 523 nanometers.

4. A system as defined in claim 1 in which said optical receiver comprises:

an optical detection subsystem for detecting focused fluorescent light components and generating a signal in response thereto for coupling to said control subsystem; and focusing optics for receiving at least a portion of said fluorescent light components from said volume and focusing said portion onto said optical detection subsystem as said focused fluorescent light components.

5. A system as defined in claim 4 in which said focusing optics also receive other light components from said volume and said optical detection subsystem further includes an optical filter for filtering said other light components.

6. A system as defined in claim 5 wherein said optical receiver further comprises an optical collection subsystem for collecting said portion of said fluorescent light components and directing said collected fluorescent light components to said focusing optics.

7. A system as defined in claim 6 wherein said light source comprises a selected one of a frequency doubled NdYAG laser having a wavelength of approximately 532 nanometers and a frequency-doubled NdYLF laser having a wavelength of approximately 523 nanometers.

8. A system as defined in claim 4 in which said optical detection subsystem comprises a spectrometer.

9. A method for remotely detecting organic material in a volume in situ, said method comprising the steps of:

generating a laser light beam and directing the generated beam at said volume in a specified direction;

detecting at an optical receiver, if organic material is present in said volume, fluorescent light components from said volume generated by said organic material in response to the laser light beam incident thereon;

localizing said organic material within said volume by a combination of information on the direction of the generated beam, a field of view of the optical receiver and timing of the detected fluorescent light components; and coupling said generating and detecting steps through a control subsystem.

10. A method as defined in claim 9 in which said laser light beam generating step includes the steps of:

generating a laser beam; and focusing said laser beam as said laser light beam on said volume.

11. A method as defined in claim 10 in which said laser beam is generated at a wavelength of approximately 523 to 532 nanometers.

12. A method as defined in claim 9 in which said detection step comprises the steps of:

detecting focused fluorescent light components and generating a signal in response thereto to said control subsystem; and receiving at least a portion of said fluorescent light components from said volume and focusing said portion for detection.

13. A method as defined in claim 12 in which said light received from said volume also includes other light components, the method further comprising the step of filtering said other light components prior to said detection step.

14. A method as defined in claim 12 in which a spectrometer is used in said detection step.

* * * * *